United States Patent
Starck et al.

(10) Patent No.: US 6,497,723 B1
(45) Date of Patent: Dec. 24, 2002

(54) STENT FOR TRANSLUMINAL IMPLANTATION

(75) Inventors: Bernd Starck, Ötisheim; Robert Alter, Neubiberg, both of (DE)

(73) Assignee: Micro Science Medical AG (DE)

( * ) Notice: Subject to any disclaimer, the term of this patent is extended or adjusted under 35 U.S.C. 154(b) by 0 days.

(21) Appl. No.: 09/486,794

(22) PCT Filed: Sep. 5, 1998

(86) PCT No.: PCT/EP98/05651

§ 371 (c)(1),
(2), (4) Date: May 22, 2000

(87) PCT Pub. No.: WO99/12495

PCT Pub. Date: Mar. 18, 1999

(30) Foreign Application Priority Data

Sep. 9, 1997 (DE) ..................................... 297 16 117 U

(51) Int. Cl.⁷ .................................................. A61F 2/06
(52) U.S. Cl. ...................................... 623/1.15; 623/1.17
(58) Field of Search ................................ 623/1.1, 1.12, 623/1.15, 1.17, 1.18

(56) References Cited

U.S. PATENT DOCUMENTS 5,697,971 A * 12/1997 Fischell et al. .............. 623/1.1

FOREIGN PATENT DOCUMENTS

| DE | 297 01 758 | 3/1997 |
| DE | 297 02 671 | 4/1997 |
| WO | 95 31945 | 11/1995 |

* cited by examiner

*Primary Examiner*—David O. Reip
*Assistant Examiner*—Julian W. Woo
(74) *Attorney, Agent, or Firm*—Cantor Colburn LLP

(57) ABSTRACT

The invention relates to a stent for transluminal implantation in a hollow organ, comprising a plurality of circumferentially interconnected stent members forming at least two chains. The chains are linked together via several intermediate members having at least a section disposed at a slant angle relative to the stent longitudinal axis, in order to compensate, at least partly, for the longitudinal shortening upon expansion of the stent. This longitudinal shortening, occurring during stretching of the stent, is reduced owing to the provision, between the chains which are close to the first stent members and linked by intermediate members, of at least one other stent member having a higher elastic deformability than the first stent members.

12 Claims, 2 Drawing Sheets

STENT FOR TRANSLUMINAL IMPLANTATION

TECHNICAL FIELD

This invention relates to a stent for the transluminal implantation in tubular organs, especially blood vessels, the said stent comprising an essentially tubular body which is modifiable from a compressed state having a first given diameter to an expanded state with an enlarged diameter, a first set of several circumferentially connected basic expansion elements forming at least two chains, several intermediate elements which serve to connect expansion elements of neighboring chains and which incorporate at least one section extending at an angle relative to the longitudinal axis of the stent so as to compensate at least in part for the reduction in length of the stent upon its expansion.

BACKGROUND OF THE INVENTION

A stent of this type has been described in EP 734 698 A2 and is used for the reopening of. pathologically changed tubular organs such as blood vessels. By way of an insertion catheter the compressed stent is introduced to the target area within the tubular organ where it is then expanded for instance by means of a special balloon catheter. The stent will remain in position in its expanded state, supporting the wall of the vessel in a manner that essentially restores the original form of the vessel. While in its compressed state the stent should be as slim as possible so as to facilitate its passage to the target area, its expanded state, by contrast, should be such that the forces generated by the expansion of the vessel can be reliably transferred yet leave the latter as flexible as possible, requirements for a stent which tend to be mutually contradictory. To compensate for the reduction in length as the stent is expanded, a reduction which is undesirable since it hinders accurate placement of the stent, the earlier document already suggests the use of intermediate elements which stretch in the longitudinal direction so that the circumferentially positioned expansion elements of the stent would remain in nearly the same location in both the compressed and the expanded states. These intermediate elements are V- or loop-shaped, permitting appropriate longitudinal expansion as the V or loop is stretched.

Still, that approach fails to adequately minimize linear contraction and the radially extended expansion elements of the stent retain their recoil effect, tending to resile into their compressed position so that in one third of all cases, despite the design concept in question, the vessels treated are blocked again within 6 months after the operation.

DE 295 21 206 U1 describes a stent in which two meander-shaped structures, one extending in the longitudinal and the other in the circumferential direction of the stent, are linked together. Loops between the two structures are designed as the intermediate elements serving to disengage the meander structures from each other. In this case as well, there is the risk of a recoil effect in that, while the loops do indeed separate the structures and to an extent accomplish a compensation for the length reduction, the structures themselves are not expanded past the point of elasticity. Moreover, the amount of structural material involved requires suitably high pressures for expanding the stent, entailing the risk of injury to the vessels.

DE 43 03 181 A1 describes a stent with circumferentially meandering structures which are directly connected only at certain points so as to ensure the necessary flexibility. Since that design does not include any intermediate elements, the stent tends to shorten as it is expanded. Because the individual meandering structures do not provide for a specific permanent expansion, the recoil effect is a factor in this case as well. Due to the evenly distributed pattern of the meandering structures the stent involved as well as those referred to earlier are flared by the so-called "trumpet effect", i.e. the ends of the stent expand to a larger diameter than does the center section as a result of which the stent is hooked at its ends into the wall of the vessel. Any linear contraction can damage the wall of the vessel, potentially defeating the intended self-healing process of the vessel.

SUMMARY OF THIS INVENTION

Against the background of such prior art, it is the objective of this invention to provide an enhanced stent of the type mentioned in which any length reduction upon expansion is minimized.

This is accomplished by providing, between the basic expansion elements of neighboring chains connected by intermediate elements, at least one additional expansion element the elastic deformability of which is greater than that of the basic expansion elements.

This stent employs intermediate elements as described in prior art, linked to basic expansion elements. However, positioned between these basic expansion elements is at least one additional expansion element with an elastic deformation coefficient greater than that of the basic expansion elements. The result is a higher level of plastic deformation of the basic expansion elements which in conjunction with the intermediate elements counteracts linear contraction. At the same time, radial expansion is ensured by the more elastic, additional expansion elements which therefore do not have to be fully deformed to the plastic level, thus retaining the necessary support strength for reliably supporting the wall of the vessel. This in turn requires no or only very little circumferential overexpansion, thus minimizing the recoil effect and consequently any complications, repeat procedures and new blockages. Overall, this stent is therefore extremely economical.

ILLUSTRATION OF PREFERRED DESIGN EXAMPLES

The following describes this invention by way of examples with reference to the attached diagrams. These are strictly examples of embodiments and are not intended to limit the inventive concept or scope to a specific physical design.

Figure 1:
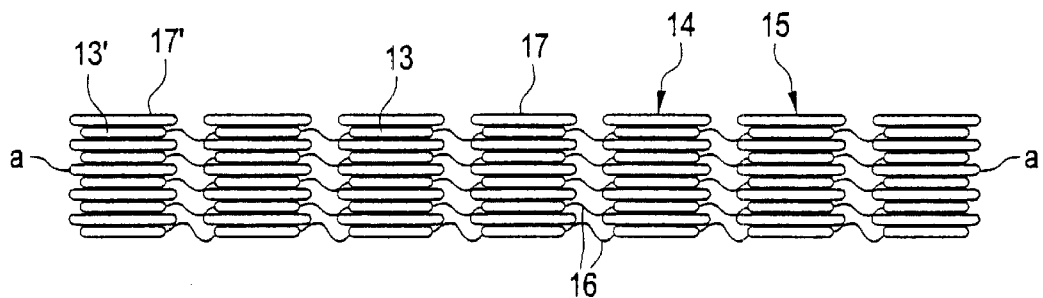
FIG. 1 Configuration of a compressed stent.
Figure 3:
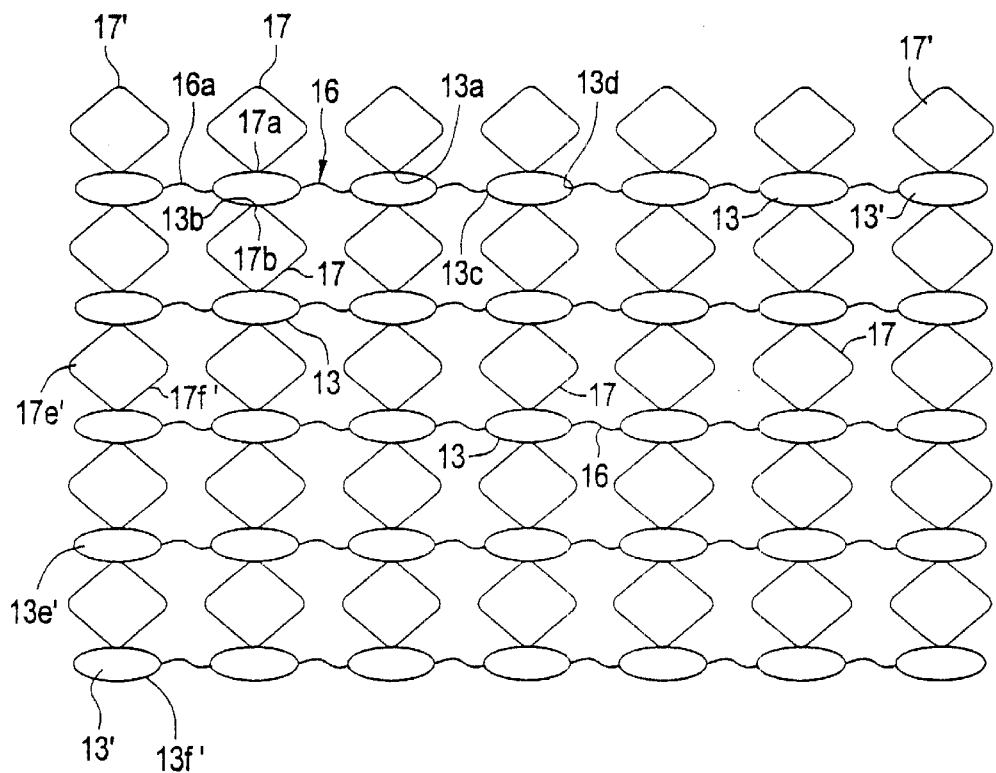
FIG. 3 Configuration of a stent in its expanded state.
Figure 2:
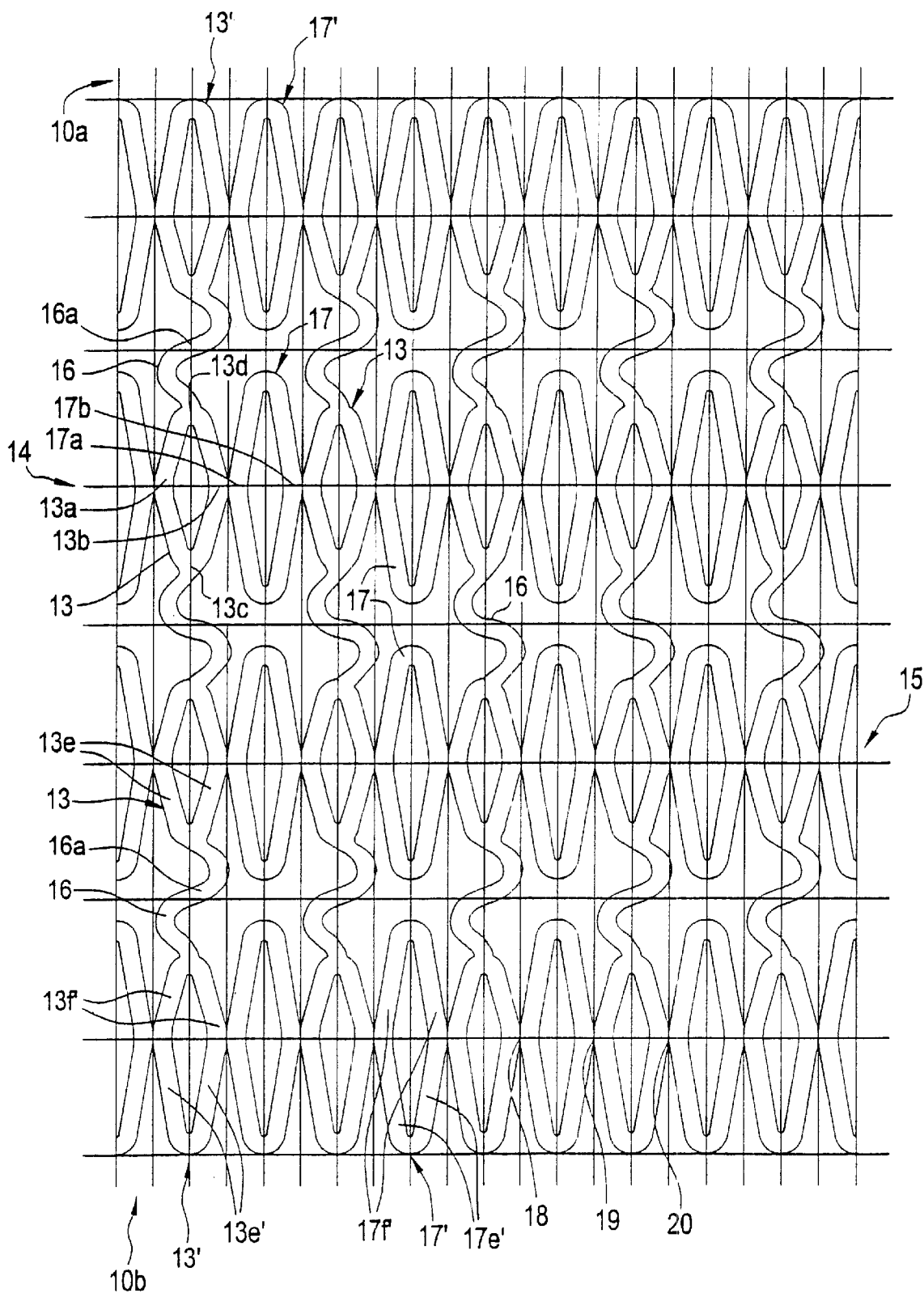
FIG. 2 Shape of a production stent.

The stent is designed for transluminal implantation in tubular organs and especially blood vessels. According to FIG. 1 it consists of an essentially tubular body which is modifiable from a compressed state with an initial diameter t into an expanded state with a larger diameter 12 as shown in FIG. 3. For explanatory purposes the figures show opened stent sections. The ex-production stent will be shaped as shown in FIG. 2. For insertion in the body it is compressed into the state shown in FIG. 1 and at the target point it is expanded (FIG. 3).

As illustrated in FIG. 2, the stent incorporates a first set of basic expansion elements 13, mutually connected in the circumferential direction, as well as additional expansion elements 17. These expansion elements form at least two chains 14, 15 which in FIG. 2 are supplemented by two end chains, discussed further below. In this example, the stent is a modular array, allowing it to be easily extended section-by-section as required in the case at hand. Several intermediate elements 16 are positioned between the chains 14, 15. These intermediate elements include at least one section 16*a* that extends at an angle relative to the longitudinal axis a—a of the stent, and serve to at least partially compensate for the linear contraction of the stent as it is radially expanded. In the expansion process, the intermediate element 16 is first stretched in the longitudinal direction and then undergoes plastic deformation to whatever extent is necessary.

The additional expansion elements 17, provided between the basic expansion elements 13 that are linked by intermediate elements 16, possess greater elastic deformability than do the basic expansion elements 13. This more or less forces a plastic deformation of the basic expansion elements which on its part helps compensate for any length reduction. The necessary functional expansion process is primarily assigned to the additional expansion elements even though, as shown in FIG. 3, the basic expansion elements are also expanded in the circumferential direction.

Higher elastic deformability of the additional expansion elements can be obtained in various ways. In the design example shown it is obtained by physical geometry in that the additional expansion elements 17, when in the compressed state, are longer in the direction of the longitudinal axis a—a than the basic expansion elements, as can be more clearly seen in FIG. 2. Since the basic expansion elements are also linked by the intermediate elements, an appropriate expansion of the intermediate elements will force a plastic deformation of the basic elements. Progressive compression of the stent is facilitated by its diamond honeycomb structure. For example, the length of a basic expansion element 13 together with the intermediate element 16 is approximately identical to the length of an additional expansion element. This contributes to the fact that the stent can support itself over nearly the entire wall of the vessel, which allows for a less bulky, highly filigreed design. Due to this filigreed structure, fewer lateral branches are blocked by excessively large ridges. The stent can be opened up with little pressure and will in fact be completely opened with a pressure as low as about 87 psi (6 bar). At the same time, by bracing itself against the entire wall of the vessel, it applies the necessary force for widening the vessel. In the expanded state, shown in FIG. 3, the length of the basic expansion elements 13 and that of the additional expansion elements 17 will be identical again in the longitudinal direction a—a.

In the design example shown in FIG. 2, the basic expansion elements 13 as well as the additional expansion elements 17 are diamond-shaped and the individual expansion elements are uniformly spaced apart. Correspondingly, the junctions 18, 19, 20 between the individual expansion elements 13, 17 are uniformly spaced apart in the circumferential direction and the width of the expansion elements is uniform in the circumferential direction. In that circumferential direction of the stent the additional expansion elements 17 feature mutually opposite corners 17*a*, 17*b* which connect to the corners 13*a*, 13*b* of the basic expansion elements 13. The other two corners of the additional expansion elements 17 are unattached, but the other two corners 13*c*, 13*d* of the basic expansion elements connect to the intermediate elements 16. Although it would be entirely possible to provide several additional expansion elements between the basic expansion elements, the design example shows an alternating array of basic expansion elements 13 and additional expansion elements 17, intended to obtain maximally uniform deformation. This link configuration produces the elongated shape of the basic expansion elements 13 shown in FIG. 3.

In FIG. 2, the corners and edges of the expansion elements 13, 17 and of the intermediate elements 16 are rounded and flow-oriented. This pattern is also maintained in the cross section so as to minimize from the start any possible complications, deposits and rejection mechanisms of the body. Any twisting of ridges is avoided and the attendant risk of injury is correspondingly reduced. The flow orientation minimizes damage to blood cells.

A closer look at the modules of the stent, identified by the dashed lines in FIG. 2, will show that the outer sections are shorter than the inner sections. This serves the purpose of using less structural material in these sections which, when the stent is deformed into its expanded state, would otherwise tend to flare outwards ("trumpet effect"). Accordingly, the outermost additional expansion elements 17' located at the ends 10*a*, 10*b* of the stent are shorter in the longitudinal direction of the stent than the inner additional expansion elements 17. It follows that the outer half 17*e*' of the outer additional expansion element 17' is shorter than its inner half 17*f*'.

In contrast thereto, the outer basic expansion elements 13' located at the ends, meaning the expansion elements which are linked to the intermediate elements 16, are longer in the longitudinal direction of the stent than the inner basic expansion elements 13. As can be seen in FIG. 2, the outer half 13*c*' of the outer basic expansion element 13' is longer than its inner half 13*f*'. The intended result in the design example shown is for the outer halves 13*e*', 17*e*' to correspond to each other in shape so as to arrive at a uniform circumferential deformation. One can expect that a coordinated deformation of the basic and the additional outer expansion elements 13', 17' will minimize a flaring of the ends 10*a*, 10*b*. Even an excessive plastic deformation will cause the ends of the stent to flare less than has been the case in prior art. Here the opposite effect is utilized, whereby a higher level of elasticity is possible even for the basic expansion elements than is the case in the inner region, thus preventing a flaring of the ends. The uniform configuration of the ends of all expansion elements enhances this effect.

In the design example shown, this effect is obtained only with the outermost expansion elements 13', 17', but it should be entirely possible to progressively widen the modular array from the ends of the stent toward the middle so as to obtain a more uniform deformation. Similarly, other shapes and configurations of the expansion and intermediate elements may be provided for as long as they ensure a corresponding coordination of plastic and elastic deformation that eliminates the shortcomings of prior-art designs.

It is self-evident that this description may be modified, altered and adapted in numerous different ways while remaining within the realm of equivalents to the attached patent claims.

What is claimed is:

1. Stent for transluminal implantation in tubular organs, especially blood vessels, comprising an essentially tubular body which is modifiable from a compressed state with an initial diameter into an expanded state with an enlarged diameter, several basic expansion elements (13) which are mutually connected and form at least two chains (14, 15), several intermediate elements (16) which connect the expansion elements (13) of neighboring chains (14, 15)

and incorporate at least one section (16a) that extends at an angle relative to the longitudinal axis (a—a) of the stent, so as to at least partially compensate for the reduction in length of the stent as it is expanded, characterized in that, between the first, basic expansion elements (13) of neighboring chains (14, 15) which are connected by intermediate elements (16), at least one additional expansion element (17) is provided the elastic deformability of which is greater than that of the basic expansion elements (13).

2. Stent as in claim 1, characterized in that, in the compressed state, the additional expansion elements (17) are of greater length in the direction of the longitudinal axis (a—a) of the stent than the basic expansion elements (13).

3. Stent as in claim 1, characterized in that, in the compressed state, the basic and the additional expansion elements (13 and 17, respectively) are diamond-shaped and the additional expansion elements (17) are connected at two corners (17a, 17b), mutually opposite in essentially the circumferential direction of the stent, to the basic expansion elements (13) whose two other diamond corners (13c, 13d) are connected to the intermediate elements (16).

4. Stent as in claim 1, characterized in that a basic and an additional expansion element (13 and 17, respectively) are positioned in alternating fashion along the circumference of the stent.

5. Stent as in claim 1, characterized in that corners and edges of the expansion elements (13, 17) are rounded and flow-oriented.

6. Stent as in claim 1, characterized in that corners and edges of the intermediate elements (16) are rounded and flow-oriented.

7. Stent as in claim 1, characterized in that the outer additional expansion elements (17') positioned at the respective end (10a, 10b) of the stent are shorter in the longitudinal direction of the stent than the inner additional expansion elements (17).

8. Stent as in claim 7, characterized in that the outer half (17e') of the outer additional expansion element (17') positioned at the end of the stent is shorter than its inner half (17f').

9. Stent as in claim 1, characterized in that the outer basic expansion elements (13') positioned at the respective end (10a, 10b) of the stent are longer in the axial direction of the stent than the inner basic expansion elements (13).

10. Stent as in claim 9, characterized in that the outer half (13e') of the outer basic expansion element (13') positioned at the end of the stent is longer than its inner half (13f).

11. Stent as in claim 8, characterized in that the outer halves (13e') of the outer basic expansion elements (13') positioned at the respective end (10a, 10b) of the stent correspond in their shape to the outer halves (17e') of the outer additional expansion elements (17').

12. Stent as in claim 1, characterized in that the junctions (18, 19, 20) between the expansion elements (13, 17) are equidistant from one another in the circumferential direction.

* * * * *